United States Patent [19]

Kelley et al.

[11] Patent Number: 5,326,398
[45] Date of Patent: Jul. 5, 1994

[54] COMPACT SLIDE SPINNER USING A DISPOSABLE SLIDE HOLDER

[75] Inventors: Thomas F. Kelley, Canton, Mass.; Larry E. Shephard, Providence, R.I.; Robert L. Scott, Medfield, Mass.

[73] Assignee: Statspin Technologies, Norwood, Mass.

[21] Appl. No.: 918,491

[22] Filed: Jul. 22, 1992

[51] Int. Cl.$^5$ .................. B05C 11/02; B05C 13/02; B05C 5/00
[52] U.S. Cl. ........................ 118/52; 118/56; 118/320; 118/501
[58] Field of Search ............. 118/56, 52, 501, 320, 118/500; 427/240; 356/36

[56] References Cited

U.S. PATENT DOCUMENTS

| | | | |
|---|---|---|---|
| 3,577,267 | 5/1971 | Preston, Jr. et al. | 118/56 |
| 3,705,048 | 12/1972 | Staunton | 118/52 |
| 3,870,014 | 3/1975 | Buck | 118/501 |
| 4,016,828 | 4/1977 | Maher, Jr. et al. | 118/6 |
| 4,031,852 | 6/1977 | Clarke et al. | 118/52 |
| 4,037,003 | 7/1977 | Maher, Jr. et al. | 427/2 |
| 4,103,643 | 8/1978 | Staunton | 118/50 |
| 4,108,109 | 8/1978 | Barger et al. | 118/52 |
| 4,197,329 | 4/1980 | Holroyd et al. | 118/52 |
| 4,209,548 | 6/1980 | Bacus | 427/2 |
| 4,266,505 | 5/1981 | Bacus | 118/699 |
| 4,280,442 | 7/1981 | Johnson | 118/52 |
| 4,294,866 | 10/1981 | Johnson | 427/2 |
| 4,349,275 | 9/1982 | Ayotte et al. | 356/36 |
| 4,468,410 | 8/1984 | Zeya | 427/2 |
| 4,633,804 | 1/1987 | Arii | 118/501 |
| 4,941,426 | 7/1990 | Sago et al. | 118/52 |
| 5,009,185 | 4/1991 | Stokes et al. | 118/56 |

Primary Examiner—W. Gary Jones
Assistant Examiner—Steven P. Griffin
Attorney, Agent, or Firm—Weingarten, Schurgin, Gagnebin & Hayes

[57] ABSTRACT

A compact slide spinner is disclosed. In the preferred embodiment, the compact slide spinner is used to prepare smears for microscopic evaluation. The spinner incorporates a disposable or reusable slide holder which encases a portion of a slide onto which the material to be smeared is placed. The holder containing the slide is then accelerated by spinning. Specimen fluid not adhering to the slide is contained within the slide holder which is discarded following preparation of the smear. Using this low-cost device, a uniform quality smear is quickly and easily prepared, while reducing the risk that laboratory personnel will be exposed to aerosol borne contagions.

14 Claims, 3 Drawing Sheets

COMPACT SLIDE SPINNER USING A DISPOSABLE SLIDE HOLDER

FIELD OF THE INVENTION

This invention relates to a device used to prepare smears for microscopic evaluation

BACKGROUND OF THE INVENTION

Various medical or scientific tests require the preparation of films on transparent slides for microscopic examination. Typically, these films or smears are prepared manually by placing a small amount of fluid, such as blood, cell culture or bone marrow suspension on a microscope slide and pushing or dragging another slide across to form a thin layer. After the slide dries and is treated with a staining solution, a laboratory technician evaluates the film under a microscope. Such manually prepared slides (wedge smears or drag smears) are very technique dependent and produce non-uniform smears or films, with one end too thick, the other end too thin. Additionally, in the case of blood films, the white blood cells are not uniformly distributed across the slide. A superior slide is produced by a slide spinner which consistently distributes a uniform monolayer of cells on a slide.

Prior art slide spinners for preparing blood films disclose a mounting platform for a slide which is able to be rapidly rotated or spun within a containment vessel. Rapid acceleration of the slide causes the blood to be evenly dispersed on the slide. During the short spin cycle excess blood is flung off the slide into the containment vessel thus forming aerosols.

Use of the prior art devices gives rise to potentially serious health risks related to aerosol borne contagions unless bulky and expensive air filtration systems are employed In addition to facilitating hazardous aerosol formation, the excess specimen flung off the slides needs to be frequently scrubbed off the containment vessel walls. Even if the containment vessel is lined with absorbent material, it quickly becomes saturated and requires frequent changing. Failure to frequently clean the vessel risks continuing biohazards and creation of a malodor. On occasion slides break, and the glass shards need to be removed along with the residue. These prior art devices thus suffer from aesthetic and biohazard deficits.

Despite having enclosed containment vessels, prior art devices allow for rapid evaporative drying of the film. Thus, care must be taken to ensure spinning is stopped requiring braking systems before the film begins to dry, otherwise there can be artifacts in the film that impair accurate reading. Any buffeting of the cell layer by air turbulence during spinning can also produce artifacts.

Also, while the prior devices may produce a uniform blood film, they do so over the entire slide. No clean area remains for handling and labeling the slide.

Finally, prior art slide spinners have incorporated the use of high power motors with large and heavy, or special purpose, armatures, and commensurately powerful braking systems. This has resulted in spinners which are large and heavy, robbing labs of valuable work space, as well as being mechanically complex, which drove the price of these devices to a point where economic considerations do not favor their use. A practical, compact, costeffective, safe and effective film preparation device has heretofore been unavailable.

SUMMARY OF THE INVENTION

The present invention is a compact slide spinner which incorporates a disposable slide holder for the preparation of a typically uniform monolayer of cells or particles on a microscope slide. This device consistently produces high quality smears at a lower cost than prior art devices while reducing the production of aerosols and liquid spattering which pose health risks to laboratory technicians.

In accord therewith, a substrate having a surface upon which a monolayer of cells from a liquified specimen is to be prepared, fits within an enclosure designed to hold the surface and retain any of the specimen spun off of the surface. In further accord therewith, the enclosure containing the surface is connected to an acceleration means which accelerates the ensemble of surface and enclosure.

In the preferred embodiment, the surface is a microscope slide which fits inside an enclosing sheath-style box having openings into which drops of blood or other fluid are introduced upon the slide in consistent locations. The box containing the slide has fittings allowing it to be secured to a platform attached to a motor, which accelerates the platform by spinning it. Following a spin cycle, a slide having a monolayer of cells covering approximately two-thirds of the slide is produced. The enclosing box, containing excess fluid, is then properly disposed of.

BRIEF DESCRIPTION OF THE DRAWINGS

Other features and benefits of the invention can be more clearly understood with reference to the specification and the accompanying drawings in which.

DESCRIPTION OF THE PREFERRED EMBODIMENT

Figure 1:
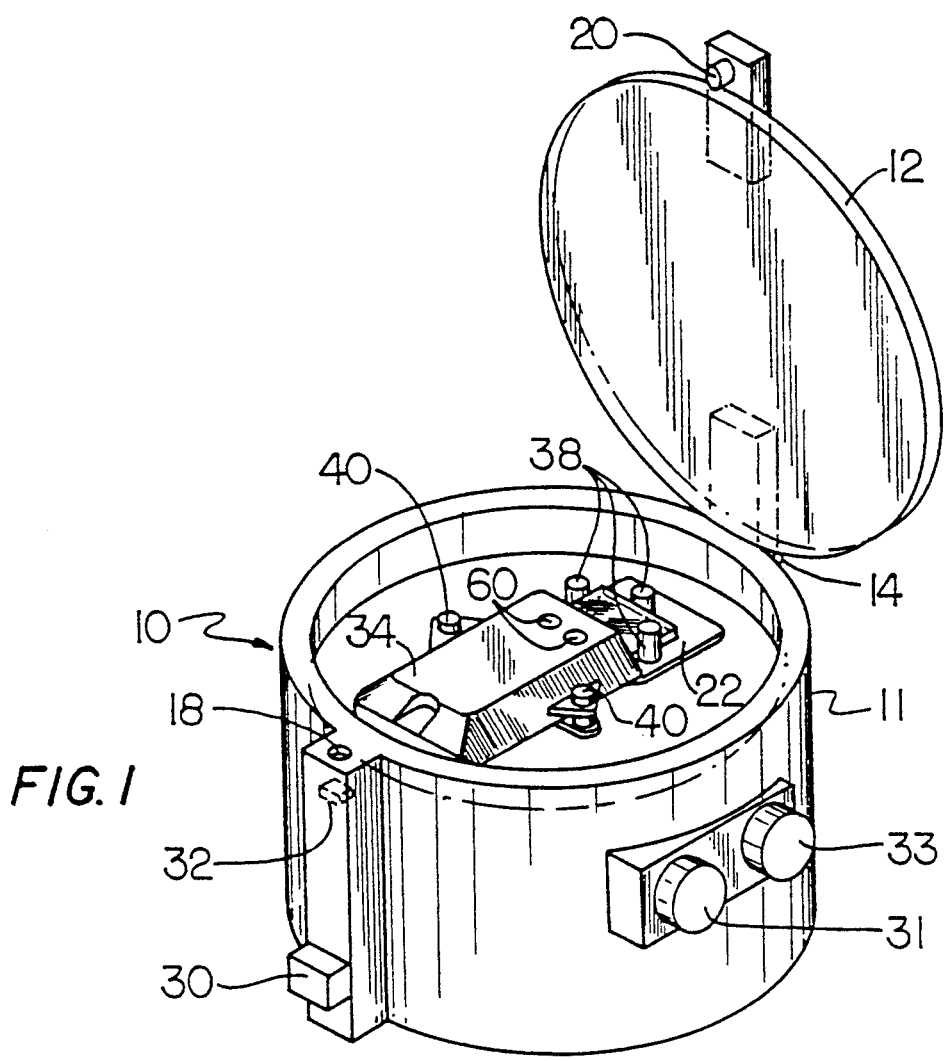
FIG. 1 is a perspective view of the compact slide spinner with mounting platform and slide holder visible.
Figure 1A:
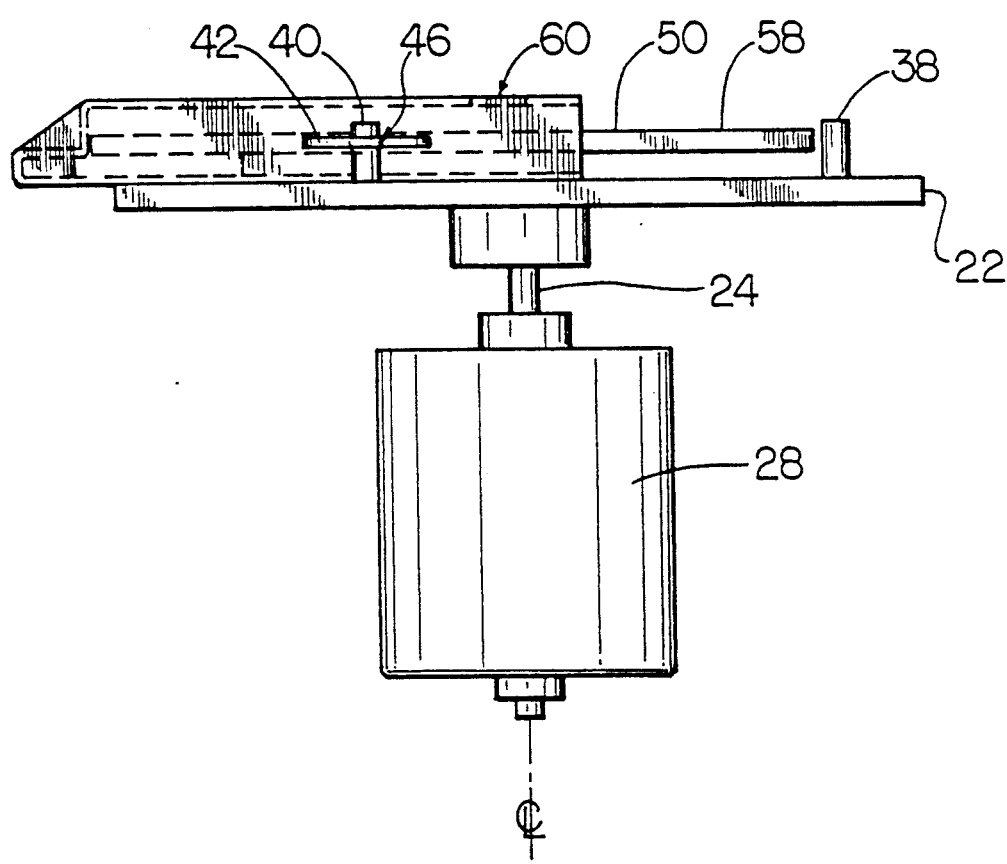
FIG. 1A is a cross-sectional diagrammatical view of a holder and motor with slide inserted.
Figure 3:
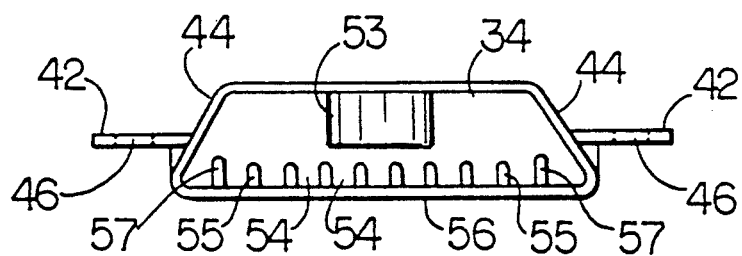
FIGS. 3, 4 and 5 are front sectional, top partially interior and side sectional views of the holder respectively.
Figure 4:
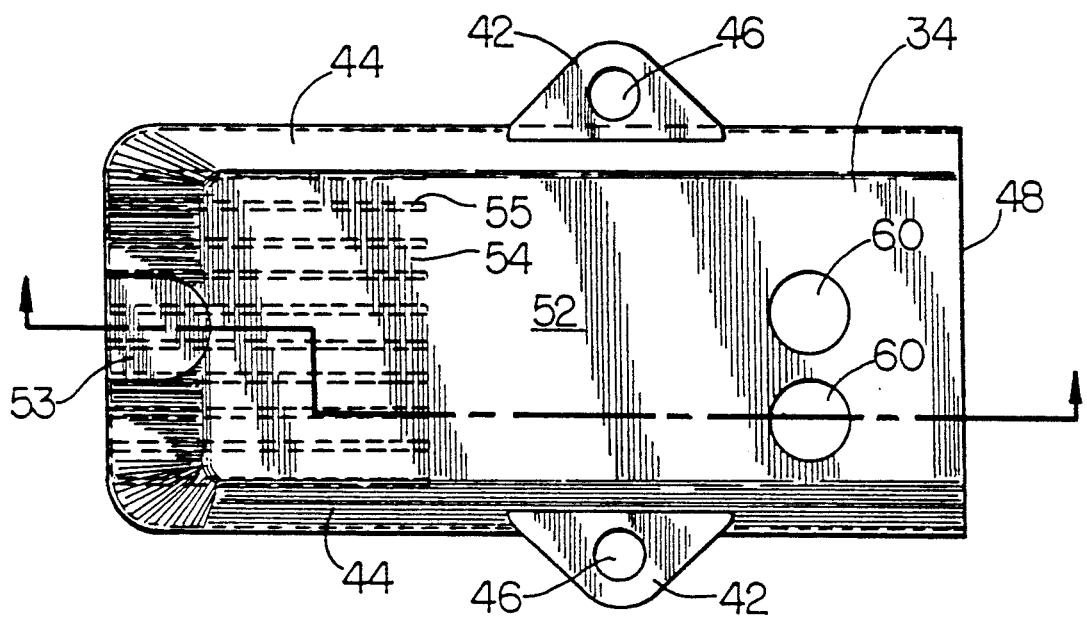
Figure 5:
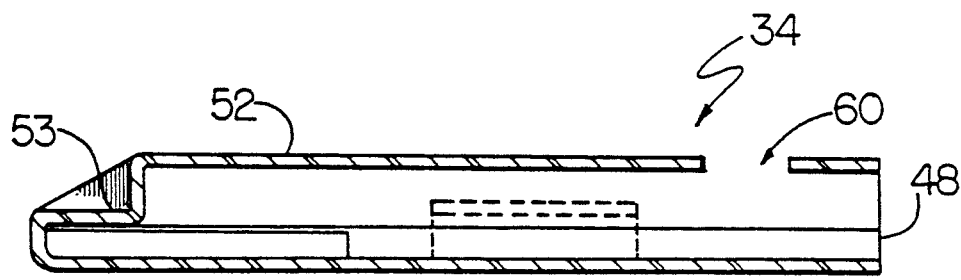

With reference now to FIGS. 1 and 1A, a compact slide spinner 10 is shown with a lid 12 shown open. The lid 12 is attached to the spinner body 11 by a hinge 14 at the rear of the spinner 10. A latch mechanism including a receiving slot 18 and mating pin 20, serves to secure the lid 12 in a closed position.

A mounting platform 22, includes a plurality of posts 38 and 40 disposed on a first surface thereof. The mounting platform is fixed on a drive shaft 24, defining an axis of rotation, which extends into the center of the body 11, and is connected to a motor 28. A power supply (not shown) is used to drive the motor 28 which has a low inertia armature. This small motor 28 allows for correspondingly smaller supporting structures and overall slide spinner 10 size.

The preferred embodiment makes use of electronic controls 31 and 33 to set variables of speeds and times of operation of the motor 28. Also incorporated are a start switch 30 and power interrupt switch 32 in slot 18 to prevent the spinner 10 from being operated with the lid 12 open.

As will be described further in conjunction with FIGS. 2-5 a slide holder 34 includes a pair Of mounting tabs 42 having holes 46 therein. The slide holder 34 is disposed on the platform 22 such that the posts 40 are disposed through the holes 46 of the mounting tabs 42 as shown.

It should be noted that here, the mounting tabs 42 (and their respective holes 46 and mounting posts 40) are disposed above and behind the center of gravity of the slide 50 and holder 34 combination. Thus unless a part fails (e.g breaks, fractures or the like) the slide 50 and holder 34 will not dislodge during spinning.

It would be desirable to minimize the rotating mass created by the platform 22, slide holder 34 and slide 50. Ideally, the holder 34 and the slide 50 disposed therein should be spun via a technique which contributes relatively little mass to the rotating assembly. Conventional mounting platforms contribute significant mass especially to the outside, of the spinning assembly which is especially disadvantageous since this makes it more difficult to spin the assembly. Thus a larger, more powerful motor is required to spin the assembly.

In the present invention however, the slide holder 34 and slide 50 are almost suspended, and there is minimum-support, and therefore mass, needed under the spinning slide 50 and its holder 34. This is especially advantageous since there is relatively little mass except the slide 50 and holder 34 at the outside or outer rim of the spinning assembly.

While the following describes the preparation of blood films, the spinner 10 may of course be used to provide thin films of other fluid specimens including but not limited to bone marrow suspensions and cell cultures.

Figure 2:
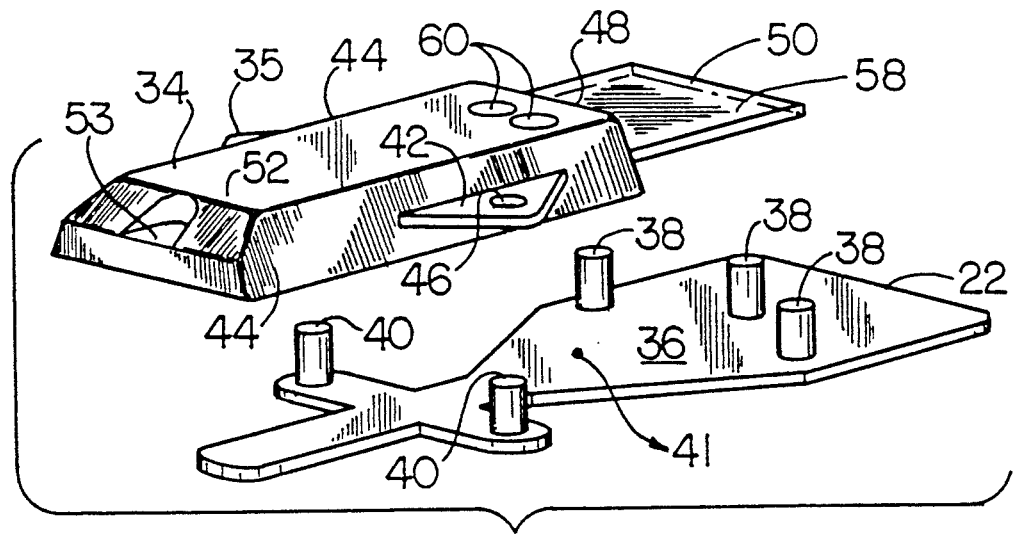
FIG. 2 is a perspective view of the mounting platform and disposable slide holder with slid inserted.

With reference now to FIG. 2, the mounting platform 22 is shown with a disposable slide holder 34. The mounting platform 22 comprises a base 36, three (two lateral and one end) retaining posts 38, two mounting posts 40, and is dimensioned such that with the disposable slide holder 34 and slide in position, the distribution of mass with respect to the center of balance 41 and axis of rotation is roughly equal. It is envisaged, however, that the mounting platform 22 can take any form suitable for the attachment of a container holding or encasing a microscope slide.

With reference to FIGS. 2, 3, 4 and 5, the disposable slide holder 34 approximates a rectangular box in appearance. The holder 34 has two mounting tabs 42, protruding from the sides 44 of the holder 34, each having a hole 46 which corresponds to the spacing of the mounting posts 40 (FIG. 2) and are mounted thereon. The holder 34 could as easily be attached with clips or bands. One end of the holder 34 has an aperture 48 into which a slide 50 (FIG. 2) is introduced. A stop 53 properly locates the slide 50 for consistent operation. The top 52 of the holder 34 has two holes 60 allowing the blood specimen to be placed on an outer third of the slide 50 after the slide 50 is positioned in the holder 34. It is envisaged that blood can be deposited on the slide 50 either before insertion into the holder 34 or via an opening in the holder 34 suitable to insert the blood specimen.

While the slide holder 34 can be as simple as a clear plastic box with an opening, the present invention incorporates several performance enhancing features of particular interest. A series of grooves or channels 54 formed by ribs 55 are located in the bottom 56 of the holder 34 which serve to support and correctly position the slide 50, and to catch and retain blood spun from the slide 50 during spinning. Side ribs 57 (FIG. 3) may be provided that are higher and longer and support the slide 50 over most of its length.

The compact slide spinner 10 (FIG. 1) and disposable slide holder 34 can be better understood by a description of the devices in operation. To prepare a blood smear, a clean slide 50 is inserted into the disposable slide holder 34 via the aperture 48, with a frosted or label edge, if any, remaining outside of the holder 34. The holder 34, with the slide 50 disposed therein, is then placed onto the mounting platform 22 by placing the mounting holes 46 in the tabs 42 on the sides 44 of the slide holder 34, over the mounting posts 40 and pressing down gently until the holder 34 comes to rest flush on top of the mounting platform 22. The labeled end 58 of the slide 50 should come to rest between the retaining posts 38 on the mounting platform 22. The slide 50 is thus positioned normal to the drive shaft 24 as illustrated in FIG. 1A.

Next, a transfer pipette (not shown) is used to place a single drop of specimen fluid such as blood (not shown) for example, through each of the two holes 60 on the top 52 of the slide holder 34 onto slide 50. The two drops of blood (not shown) pool together to ensure uniform coverage on the slide 50. This normally takes one or two seconds. No blood need remain on the outside of the slide holder 34. The slide 50 is then spun immediately after adding the blood.

To start the spin cycle, lid 12 (FIG. 1) of the spinner 10 (FIG. 1) is closed, engaging the latch mechanism (FIG. 1). The operator then activates the start switch 30 (FIG. 1). Then, depending on the previously selected speed setting, the holder 34 is accelerated to 1,500 to 3,000 rpm and stops quickly because of its low inertia. Depending on the previously selected time setting, the entire running time is 0.4 to 3.0 seconds. Despite using a much smaller motor 28 (FIG. 1), and attaining a lower final rotational speed than prior art devices, the compact slide spinner 10 (FIG. 1) achieves the desired result of a uniform monolayer blood smear. By placing the blood specimen farther from the axis of rotation, an effective acceleration rate similar to that undergone in the prior art units using larger motors, attaining up to 6,000 rpm, is achieved.

When the spinner 10 (FIG. 1) comes to a stop the latch mechanism (FIG. 1) can be disengaged, the lid 12 (FIG. 1) is opened, and the slide holder 34 with slide 50 is removed. The slide 50 is then withdrawn and processed in accordance with standard laboratory procedure. The slide holder 34 is subsequently disposed in a manner which reflects the nature of the material contained inside. The holder 34 may thus be low-cost and disposable. Alternatively, under appropriate conditions the holder 34 may be sanitized and reused. When spun in this fashion, the slide 50 will have a blood smear covering approximately two-thirds of one side of the slide 50. The remaining surface area of the slide 50 is free from blood and is suitable for labeling and handling.

These and other examples of the concept of the invention illustrated above are intended by way of example and the actual scope of the invention is to be determined solely from the following claims.

We claim:

1. A device for preparing a thin film from a fluid specimen placed upon a substrate comprising:
    an enclosure for receiving said substrate and covering said fluid specimen during preparation of said thin film, said enclosure including a top, a bottom, and a plurality of sides joining said top to said bottom, at least one of said sides including an opening to receive at least a portion of said substrate therethrough, said top covering said fluid specimen on said substrate; and
    a spinner for spinning said enclosure and said substrate received therewithin.

2. The device of claim 1 wherein said substrate is a microscope slide.

3. The device of claim 1 wherein said enclosure has a stop to position said substrate.

4. The device of claim 1 wherein said enclosure include a plurality of ribs within said enclosure for supporting said substrate and providing an excess specimen receiving depression.

5. The device of claim 1 wherein said top of said enclosure includes an aperture through which said specimen is introduced into said enclosure.

6. The device of claim 1 wherein said spinner includes means for spinning said enclosure and means for braking said enclosure.

7. The device of claim 6 wherein said means for spinning includes a motor.

8. The device of claim 6 wherein said enclosure is spun about an axis of rotation that is normal to said substrate.

9. The device of claim 6 wherein said spinner includes a mounting platform adapted to retain said enclosure thereon.

10. The device of claim 9 wherein said platform includes a plurality of posts and said enclosure includes a plurality of mounting holes, said plurality of posts matable with said plurality of mounting holes of said enclosure.

11. An enclosure for use in preparing thin films of a fluid specimen on a microscope slide, comprising:
    a top;
    a bottom; and
    a plurality of sides joining said top to said bottom, at least one of said sides including an opening to receive at least a portion of said microscope slide therethrough, said top covering said fluid specimen on said microscope slide; and
    means for collecting excess specimen from said microscope slide during spinning.

12. The enclosure of claim 11 further including means for positioning said enclosure on a spinner.

13. The enclosure of claim 11 wherein said enclosure includes ribs defining said means for collecting.

14. An enclosure for preparing a thin film on a substrate utilizing a fluid specimen to prepare said thin film, said enclosure positionable on a mounting platform coupled to a spinner, said mounting platform having a plurality of mounting posts for retaining said enclosure thereon, said enclosure comprising:
    a disposable sheath having an open end, a closed end, an aperture for admitting said fluid specimen into said disposable sheath, and a plurality of apertures cooperative with said plurality of mounting posts for positioning said sheath upon said mounting platform;
    means for receiving said substrate through said open end and for positioning said substrate in said sheath;
    means for collecting excess specimen from said substrate during spinning.

* * * * *